United States Patent [19]

Grandjean

[11] Patent Number: 5,098,442
[45] Date of Patent: Mar. 24, 1992

[54] MUSCLE CONTRACTION CONTROL BY INTRAMUSCULAR PRESSURE MONITORING

[75] Inventor: Pierre-Andre Grandjean, Bassenge, Belgium

[73] Assignee: Medtronic, Inc., Minneapolis, Minn.

[21] Appl. No.: 446,811

[22] Filed: Dec. 6, 1989

[51] Int. Cl.$^5$ ............................................. A61M 1/10
[52] U.S. Cl. ........................................ 623/3; 600/16
[58] Field of Search .................. 623/3; 600/16, 17, 18

[56] References Cited

U.S. PATENT DOCUMENTS

| 4,143,661 | 3/1979 | LaForge et al. ............... 128/419 R |
|---|---|---|
| 4,384,829 | 5/1983 | Conley et al. ........................ 623/3 |
| 4,453,537 | 6/1984 | Spitzer ................................. 600/17 |
| 4,457,673 | 7/1984 | Conley et al. ........................ 623/3 |
| 4,666,443 | 5/1987 | Portner ............................... 500/16 |
| 4,685,446 | 8/1987 | Choy ................................... 600/18 |
| 4,771,765 | 9/1988 | Choy et al. .......................... 600/18 |

FOREIGN PATENT DOCUMENTS 216042  4/1987  European Pat. Off. .............. 600/16

*Primary Examiner*—Randy Citrin Shay
*Attorney, Agent, or Firm*—John L. Rooney

[57] ABSTRACT

A technique for monitoring the performance of a skeletal muscle used in a cardiac assist sytem. The skeletal muscle is surgically wrapped about the heart, the descending aorta, or a chamber connected in series with or parallel to the descending aorta to provide direct assistance when electrically stimulated to correspond with naturally or artifically paced heart contractions. An alternate system provides indirect assistance by improving coronary perfusion when the skeletal muscle is electrically stimulated to contract about an artificial chamber during relaxation of the myocardium. In either type or cardiac assist system, the skeletal muscle must be conditioned to perform constant contraction/relaxation within the range of normal heart rates. This conditioning occurs over a length of time which is too long to be directly managed by medical personnel in a sterile environment except experimentally. The present invention provides apparatus and techniques for managing the conditioning process automatically. The same apparatus and techniques are applicable to many other functions involving real time monitoring to include coordinating the timing of skeletal muscle contraction with myocardial contractions. Such other functions are muscle contraction monitoring, muscle pacing threshold determination and monitoring, and muscle contraction timing analysis for improving biomechanical efficiency.

9 Claims, 8 Drawing Sheets

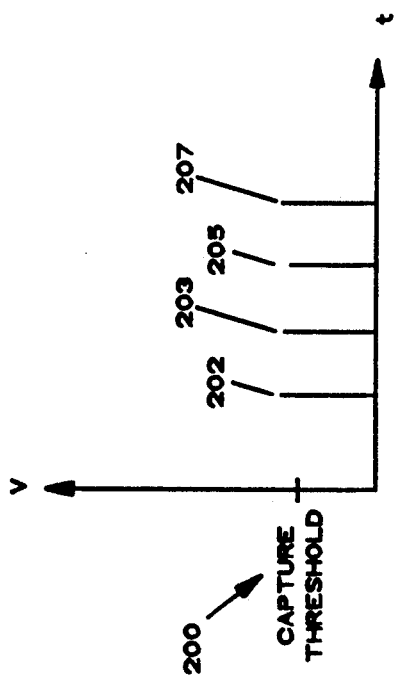
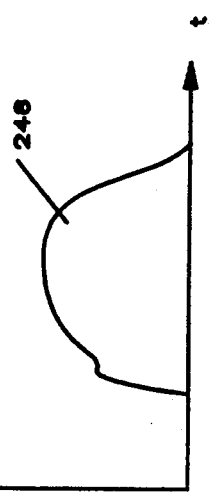
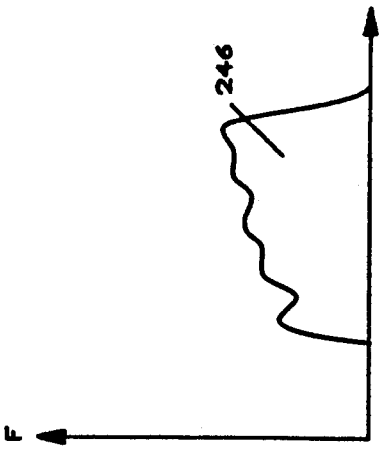
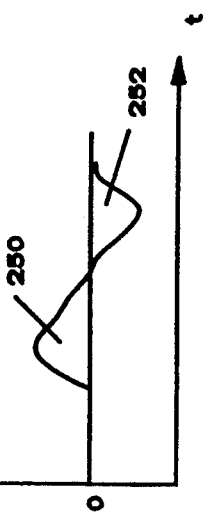

MUSCLE CONTRACTION CONTROL BY INTRAMUSCULAR PRESSURE MONITORING

CROSS REFERENCES TO CO-PENDING APPLICATIONS

This application is related to Ser. No. 07/446,953, Filed Dec. 6, 1990, pending, entitled "Muscle Fitness Detection by Colorimetry" by the same assignee; Ser. No. 07/446,952, Filed Dec. 6, 1990, pending, entitled "Muscle Output Monitor by Intramuscular Temperature Variation Measurement" by the same assignee; and Ser. No. 07/446,594, Filed Dec. 6, 1990, pending, entitled "Steroid Eluting Intramuscular Lead" by the same assignee.

BACKGROUND OF THE INVENTION

1. Field of the Invention

The present invention relates generally to electrical muscle stimulation, and more particularly, relates to systems for monitoring performance of the skeletal muscle in cardiac assist systems powered by skeletal muscle.

2. Description of the Prior Art

Cardiac assist systems do not replace the human heart, but merely supplement it. Many techniques have been proposed using a variety of mechanical power sources. Typically these require some form of percutaneous energy transfer because of the difficulty in storing sufficient energy subcutaneously. Such systems are cumbersome and inconvenient for the patient and are prone to infection along the percutaneous energy transfer path.

A technique holding a great deal of promise is to power the cardiac assist system from a surgically modified skeletal muscle. The cardiac assist system is thus powered by normal biochemical processes. U.S. Pat. No. 4,813,952 issued to Khalafalla teaches a number of configurations of a skeletal muscle powered cardiac assist system.

One problem peculiar to a skeletal muscle powered cardiac assist system is that the skeletal muscle must be conditioned to the constant load of continuous contraction/relaxation demanded of the myocardium. U.S. Pat. No. 4,411,268 issued to Cox teaches a technique for conditioning the skeletal muscle. Whereas the apparatus of Cox is effective to accomplish this conditioning, his system has no provisions for feedback to permit the self-regulation of the conditioning regimen. In practice this necessitates the attention of highly skilled medical personnel to monitor the conditioning process with sophisticated instrumentation and to manually control the stimulation regimen with pulse generator programming equipment. Furthermore, neither Cox nor Khalafalla teach a real time feedback mechanism, whereby optimal timing between myocardial contraction and skeletal muscle contraction can be established and verified.

A second problem is basic monitoring of the skeletal muscle contractions. This is important because it provides a way to check and modify various pulse generator timing and amplitude parameters. Currently, the prior art suggests no effective means for performing this monitoring function.

SUMMARY OF THE INVENTION

In the preferred mode, a chronically biocompatible pressure transducer is implanted within the skeletal muscle tissue. This transducer produces electrical signals sufficient to enable an implantable pulse generator to measure the timing and extent of contraction and relaxation of the skeletal muscle in the performance of cardiac assist.

The timing indications are important because they permit the implantable pulse generator to stimulate the skeletal muscle at the appropriate time to optimize the assist. For a configuration wherein the skeletal muscle is wrapped about the aorta, for example, contraction of the skeletal muscle should be delayed until immediately following contraction of the myocardium. Contraction of the skeletal muscle during the contraction of the myocardium will increase rather than decrease the load on the human heart. For skeletal muscle wrapped directly about the human heart, the stimulation should cause simultaneous contraction to achieve maximum benefit.

Measurement of timing and extent of skeletal muscle contractions permits the implantable pulse generator to monitor and control the conditioning regimen. This is important from a system viewpoint as it permits efficient energy utilization, as various phases of the conditioning process require the use of substantial stimulation energy. Such monitoring and control are important medically because prior to complete conditioning, the skeletal muscle will readily fatigue, possibly resulting in excess loading of the myocardium.

The present invention substantially improves the efficiency of the cardiac assist system through monitoring and control of the conditioning activity. Such monitoring and control also decreases the medical risk of the procedure.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 7A is a graph of stimulation signals applied to the conditioned muscle.

FIG. 7B is the contraction pattern resulting from the stimulation of FIG. 7A.

FIG. 7C is the waveform of the contraction as viewed by the pressure sensor.

FIG. 7D is the differentiated pressure sensor signal showing that the skeletal muscle is fully conditioned.

DETAILED DESCRIPTION OF THE PREFERRED EMBODIMENTS

The preferred embodiments of the present invention are cardiac assist systems which are powered by surgically altered skeletal muscles. For a detailed description of a number of different configurations for such a system, please consult U.S. Pat. No. 4,813,952 issued to Khalafalla which is herein incorporated by reference.

Figure 1:
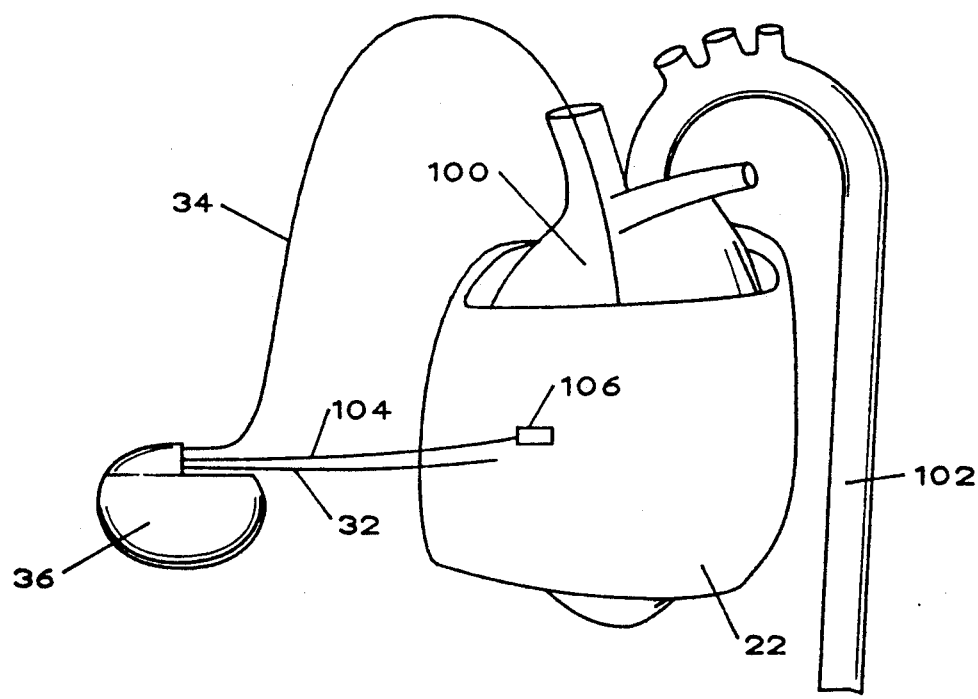
FIG. 1 is a first embodiment of the present invention wherein the skeletal muscle is wrapped about the myocardium.

FIG. 1 is a plan View of one embodiment of the present invention. Human heart 100 has been surgically wrapped with skeletal muscle 22 in the manner known in the art. In this configuration skeletal muscle 22 is electrically stimulated to contract at the same time as the myocardium of human heart 100, thereby increasing blood flow through ascending and descending aorta 102. Stimulation of skeletal muscle 22 occurs via implantable pulse generator 36 which transfers stimulation pulses to skeletal muscle 22 via electrical lead 32. Synchronization with human heart 100 occurs because implantable pulse generator 36 senses the electrical activity of human heart 100 via transveneous lead 34 and provides artificial pacing pulses as required in the mode of a common demand pacemaker. Lead 104 directs the output of pressure sensor 106 to implantable pulse generator 36. Pressure sensor 106 is imbedded in skeletal muscle 22. It senses the timing and extent of the contractions of skeletal muscle 22 as described in detail below.

Figure 2:
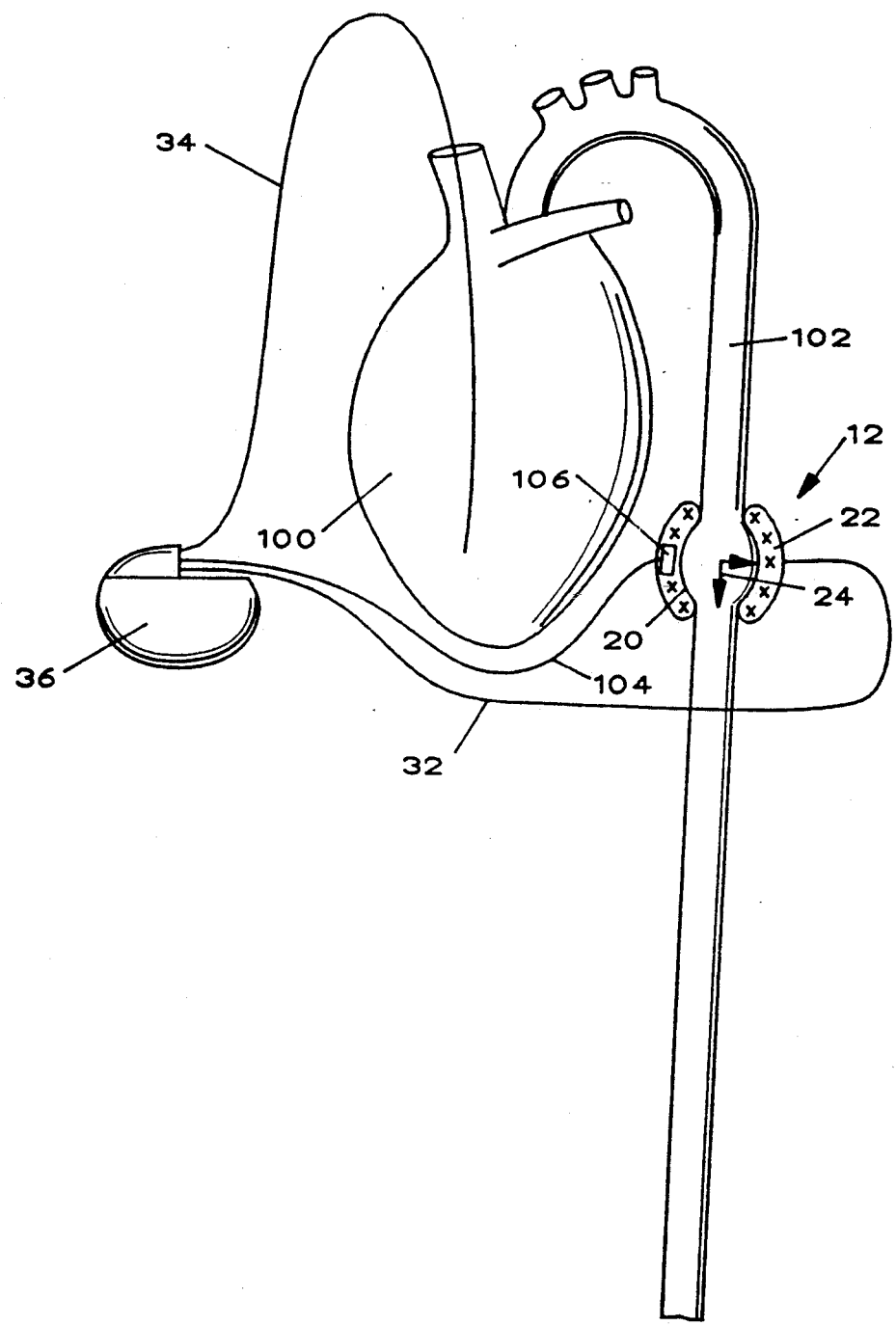
FIG. 2 is an alternative embodiment of the present invention wherein the skeletal muscle is wrapped about the descending aorta.

FIG. 2 shows an alternative cardiac assist system wherein skeletal muscle 22 is surgically wrapped about chamber 20 which is spliced into descending aorta 102. Chamber 20 is deformable by contractions of skeletal muscle 22, permitting it to exert additional pumping force. The remainder of the elements of the alternative embodiment of FIG. 2 are identical with those of FIG. 1 except the timing of stimulation to skeletal muscle 22 via electrical lead 32 is delayed. If skeletal muscle 22 were to contract at the same time as the myocardium, the load on human heart 100 would actually be increased. Therefore, implantable pulse generator 36 must delay stimulation of skeletal muscle 22 until after contraction of human heart 100 is complete as described in detail below.

Figure 3:
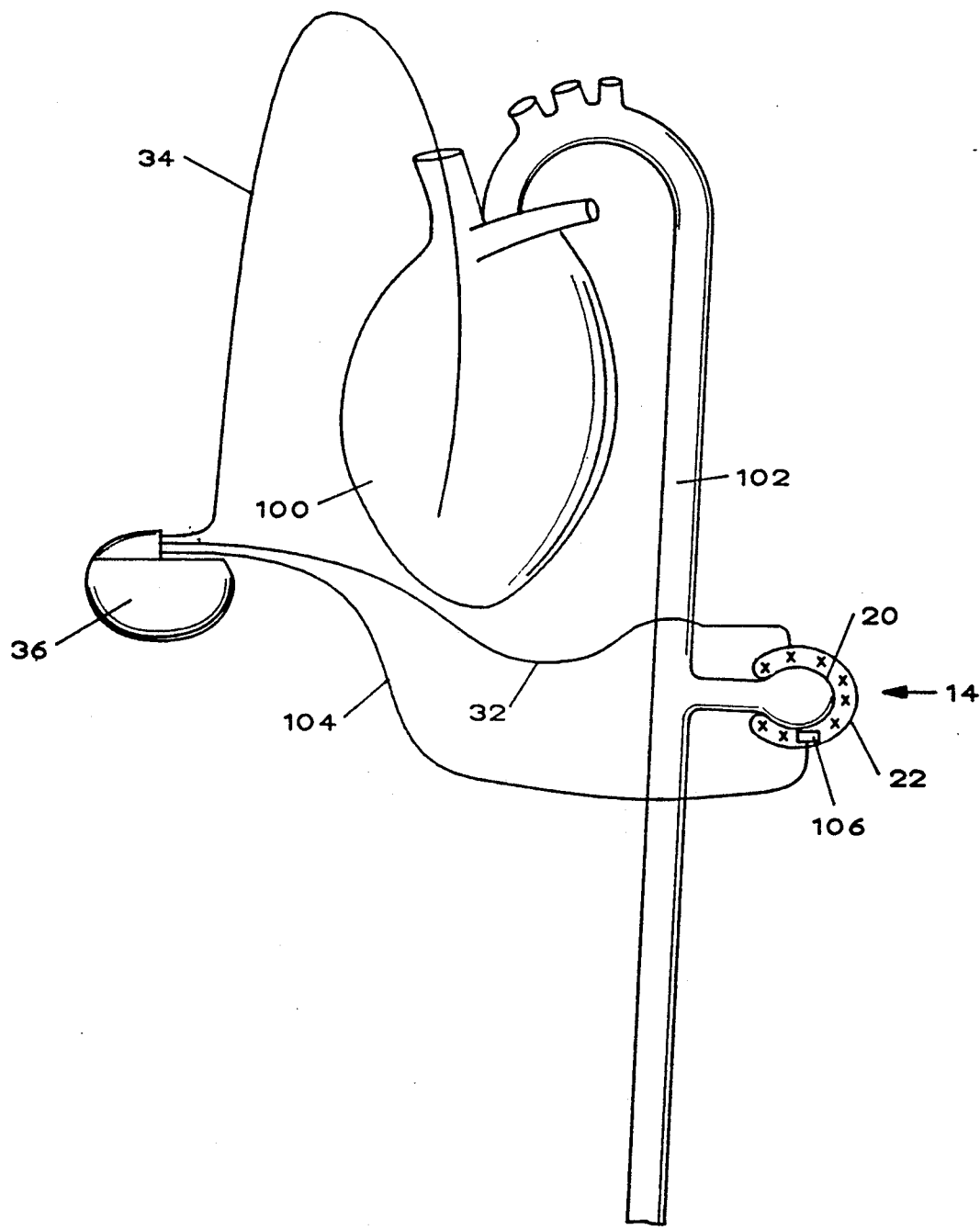
FIG. 3 is an alternative embodiment for counterpulsation of the descending aorta.

FIG. 3 shows an alternative cardiac assist system wherein skeletal muscle 22 is surgically wrapped about closed chamber 20 which is coupled to descending aorta 102. In this embodiment, implantable pulse generator 36 stimulates skeletal muscle 22 to contract upon relaxation of human heart 100 and to relax upon contraction of human heart 100. The resulting counterpulsations assist human heart 100 by increasing overall perfusion of the myocardial tissue. The remaining elements of this embodiment function as described above.

Figure 4:
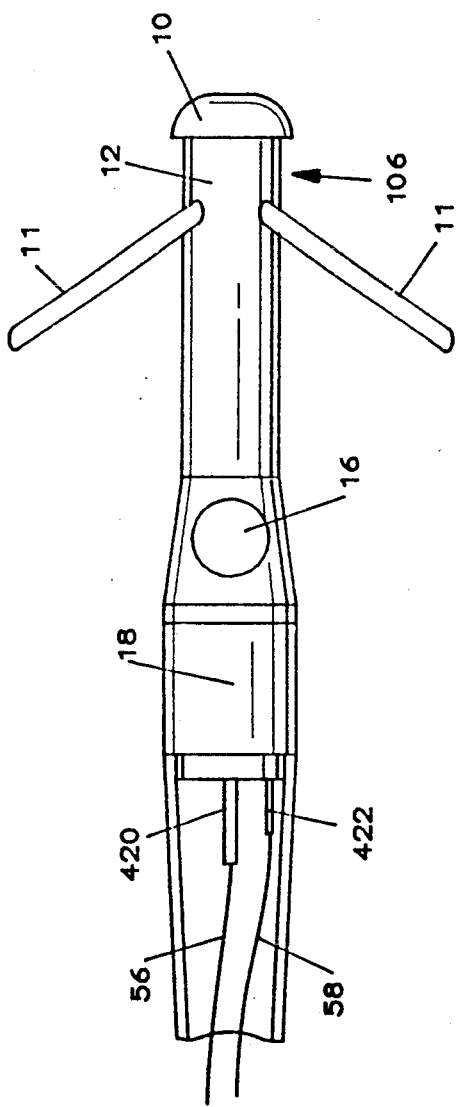
FIG. 4 is a plan view of the pressure transducer.

FIG. 4 is a plan view of pressure sensor 106. This is preferably of the type disclosed in U.S. Pat. No. 4,485,813 issued to Anderson, et al., herein incorporated by reference. The pressure sensor is piezoelectric. Piezo-resistive pressure sensors are disclosed in U.S. Pat. No. 4,407,296 issued to Anderson and U.S. Pat. No. 4,432,372 issued to Monroe, also incorporated by reference.

Pressure sensor 106 has a distal tip 10 at the end of hollow and rigid shank 12. Tines 11 are appended to aid in attachment. These work particularly well with transveneous pacing leads. However, different attachment means may be more appropriate depending upon the exact nature of the skeletal muscle used. The pressure capsule 18 is hermetically sealed. Bore 16 provides fluid communication with pressure capsule 18. Because pressure capsule 18 uses a piezoelectric element, incident forces present produce a voltage across terminals 420 and 422. This signal is coupled to implantable pulse generator 36 via conductors 56 and 58 which run the length of lead 104.

Figure 5:
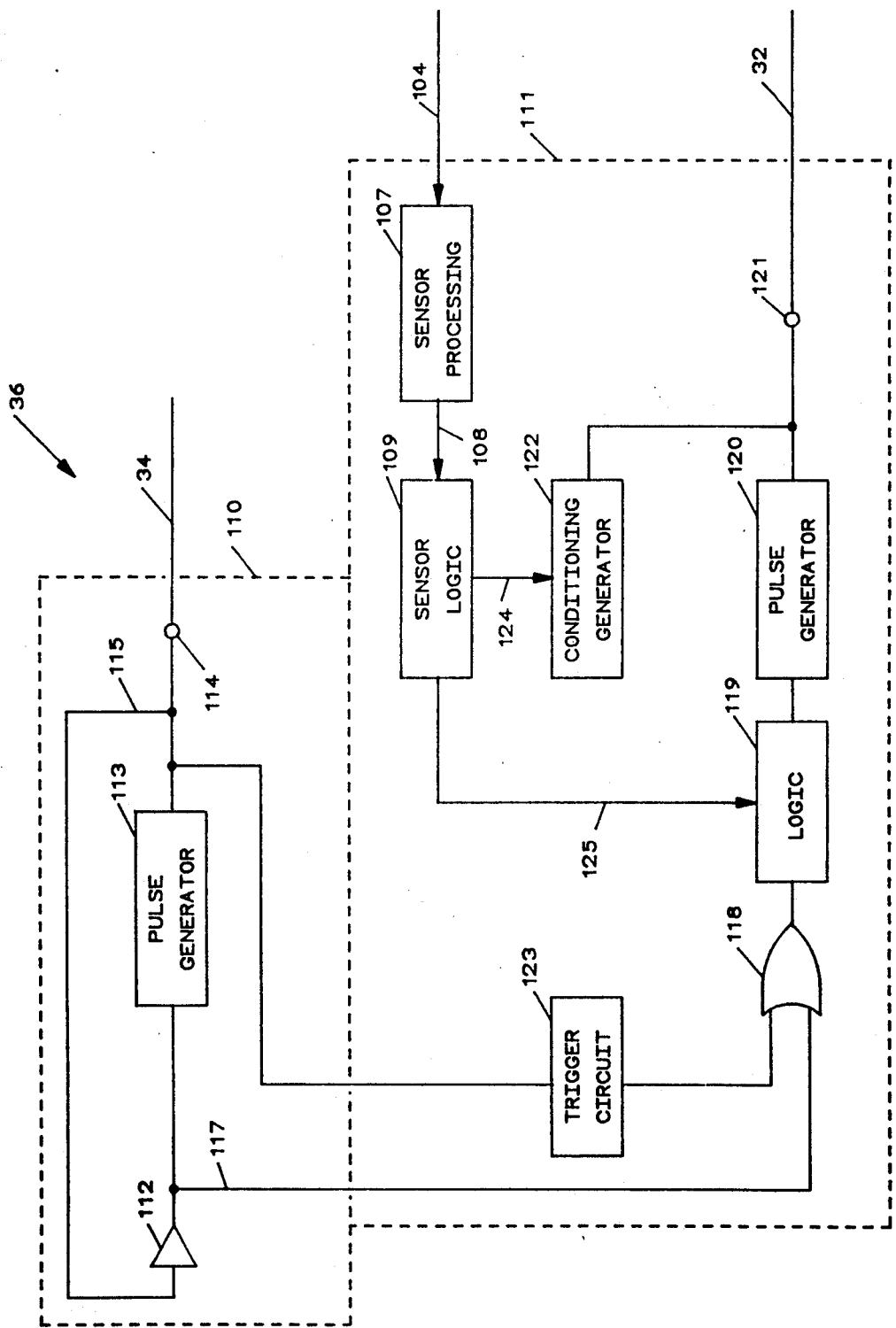
FIG. 5 is a block diagram of the implantable pulse generator.

FIG. 5 is a block diagram of implantable pulse generator 36. This element contains two basic portions. The first of these is primarily a demand pacemaker 110, which is readily known in the art. Its components include terminal 114, which couples transveneous lead 34 to sense amplifier 112 via line 115 and also directs artificial pacing pulses from pulse generator 113 to the myocardial tissue. Sense amplifier 112 attempts to detect naturally occurring heartbeats. If one is found, the artificial pacing pulse is inhibited.

Skeletal muscle 22 is coupled to implantable pulse generator 36 via terminal 121 which couples to electrical lead 32 to deliver the electrical stimulation energy. This stimulation energy is supplied by pulse generator 120. The signals used to condition skeletal muscle 22 are generated by conditioning generator 122 and supplied to terminal 121. The generation of such conditioning signals is discussed more extensively in U.S. Pat. No. 4,411,268, issued to Cox, which is incorporated herein by reference.

Feedback on the conditioning process is sensed by pressure sensor 106 and transferred to sensor processing 107 which processes the signal in a manner described below. This processed sensor signal is transferred via line 108 to sensor logic 109 which determines the degree of conditioning yet required using the technique described below. When the conditioning process is complete, sensor logic 109 notifies conditioning generator 122 via line 124 to produce the maintenance signals described below.

Sensor logic 109 also notifies logic 119 via line 125 of the timing of the actual contraction of skeletal muscle 22. This permits logic 119 to properly time the stimulation signal to skeletal muscle 22 as explained below.

Trigger circuit 123 and OR-gate 118 function as described by Cox to time the generation of the stimulation pulse to skeletal muscle 22 in relation to the contraction of human heart 100. A discussion of this timing for the various embodiments may be found below.

An alternative implementation of implantable pulse generator 36 is through the use of a microprocessor controlled general purpose implantable pulse generator such as the PROMETHEUS TM pulse generator manufactured by Medtronic, B. V. of the Netherlands. The primary advantage of such an implementation is the ease with which such a programmable device can change modes of operation. This is particularly useful when doing clinical research. A description of the use of such a device may be found in the paper "Pulse Generator for Biomechanical Cardiac Assistance by Computer Pulsation Technique", by Grandjean et al., published in the "Record of the Conference on Skeletal Muscle for Cardiac Assist and Repair, Banff, Sept. 28, 1988, Oct. 2, 1988", published by Futura Editions (August 1989).

FIG. 6 comprises FIGS. 6A, 6B, 6C and 6D which are graphical representations of stimulation pulses to and response of unconditioned skeletal muscle 22.

Figure 6A:
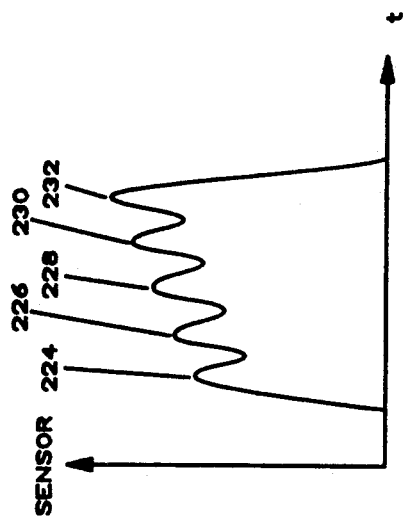
FIG. 6A is a graph of stimulation pulses applied to the unconditioned muscle.

FIG. 6A shows the stimulation patterns used to perform the conditioning. Skeletal muscle stimulation is different from cardiac stimulation in that the skeletal muscle does not have an all or nothing response to the electrical stimulus as does the myocardium. The skeletal muscle exhibits a gradual recruitment of fibers with increases in pulse amplitude and pulse width. Threshold for skeletal muscle 22 is the pulse amplitude/width needed to start muscle force recruitment. Pulse 202 is the stimulation pulse produced by pulse generator 120. It is generated to occur at the correct time in relation to the contraction of human heart 100. To be effective in causing contraction of skeletal muscle 22, pulse 202 must have a voltage greater than capture threshold 200. Pulses 204, 206, 208 and 210 are conditioning pulses produced by conditioning generator 122. The pulse rate is dependent upon the specific nature of skeletal muscle 22 as taught by Cox, but it is typically in a range of 20-30 hz. To optimally perform conditioning, pulses 204, 206, 208 and 210 have a voltage in excess of capture threshold 200.

Figure 6C:
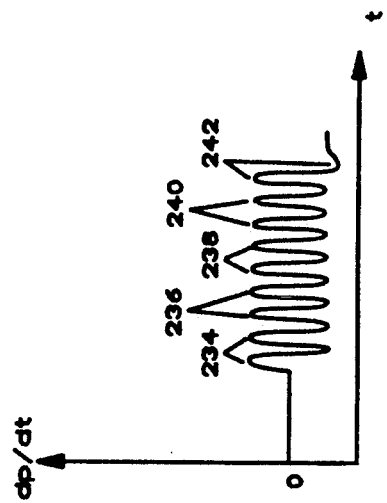
FIG. 6C is the waveform of the contraction as viewed by the pressure sensor.
Figure 6B:
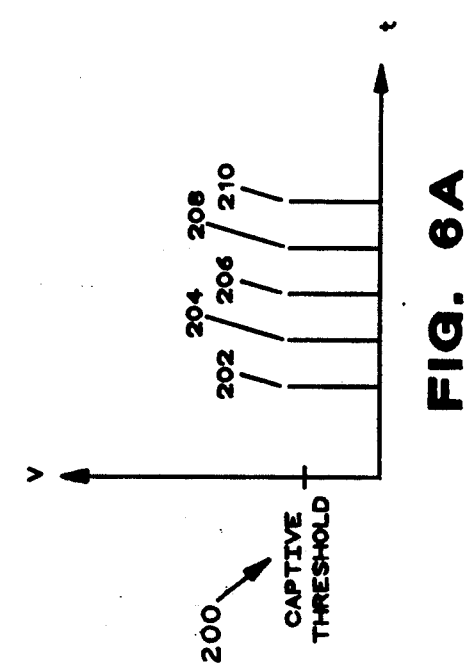
FIG. 6B is the contraction pattern resulting from the stimulation of FIG. 6A.

FIG. 6B shows the response of unconditioned skeletal muscle 22 to receipt of pulses 202, 204, 206, 208 and 210. Notice that each produces a contractile force 214, 216, 218, 220 and 222, respectively. This occurs with unconditioned muscles which are known as "fast-twitch" muscles. A more detailed explanation may be found in Cox.

FIG. 6C shows the response of pressure sensor 106 to the contractions of FIG. 6B. These result in voltage peaks 224, 226, 228, 230 and 232, respectively.

Figure 6D:
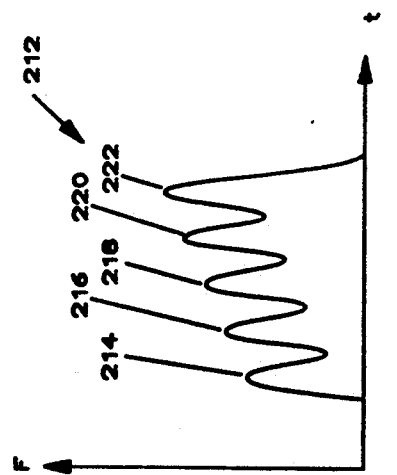
FIG. 6D is the differentiated pressure sensor signal showing that the skeletal muscle is unconditioned.

FIG. 6D shows the result of differentiation by sensor processing 107 of the sensor signal of FIG. 6C. This differentiation produces sharp peak pairs 234, 236, 238, 240 and 242, respectively, indicating the inflection points. From this waveform, a simple analog filter and detector known to those in the art could easily determine that skeletal muscle 22 is unconditioned.

FIG. 7 shows the corresponding waveforms for skeletal muscle 22 after complete conditioning. When presented with the stimulation pattern of FIG. 6A, the contractile response is shown in FIG. 7B as waveform 246. Notice that individual conditioning pulses no longer produce major contractile peaks. This occurs because skeletal muscle 22 has been conditioned to act as a "slow-twitch" muscle, similar to myocardial tissue. When the conditioned response of FIG. 7B is sensed by pressure sensor 106, the resulting waveform 248 of FIG. 7C is produced. This results in the differentiated waveform of FIG. 7D after processing by sensor processing 107. This represents but two inflection points as excursions 250 and 252. Again this becomes easily recognizable as a skeletal muscle 22 which is fully conditioned.

FIG. 7A shows the stimulation pattern used after skeletal muscle 22 is fully conditioned. Pulse 202 has a voltage in excess of capture threshold 200. This pulse which is produced by pulse generator 120 stimulates the contraction of skeletal muscle 22. Conditioning pulses 204, 206, 208 and 210 (see also FIG. 6A) produced by conditioning generator 122 have been replaced by maintenance pulses 203, 205, 207 and 209, respectively. The maintenance pulses must yet have a voltage greater than capture threshold 200. However, because of the smoother contraction pattern of the conditioned skeletal muscle, pulse width, pulse amplitude, pulse spacing and pulse number can be safely adjusted to save energy. Conditioning generator 122 switches from conditioning pulses to maintenance pulses in response to a notification of a conditioning accomplished signal from sensor logic 109 via line 124.

Figure 8:
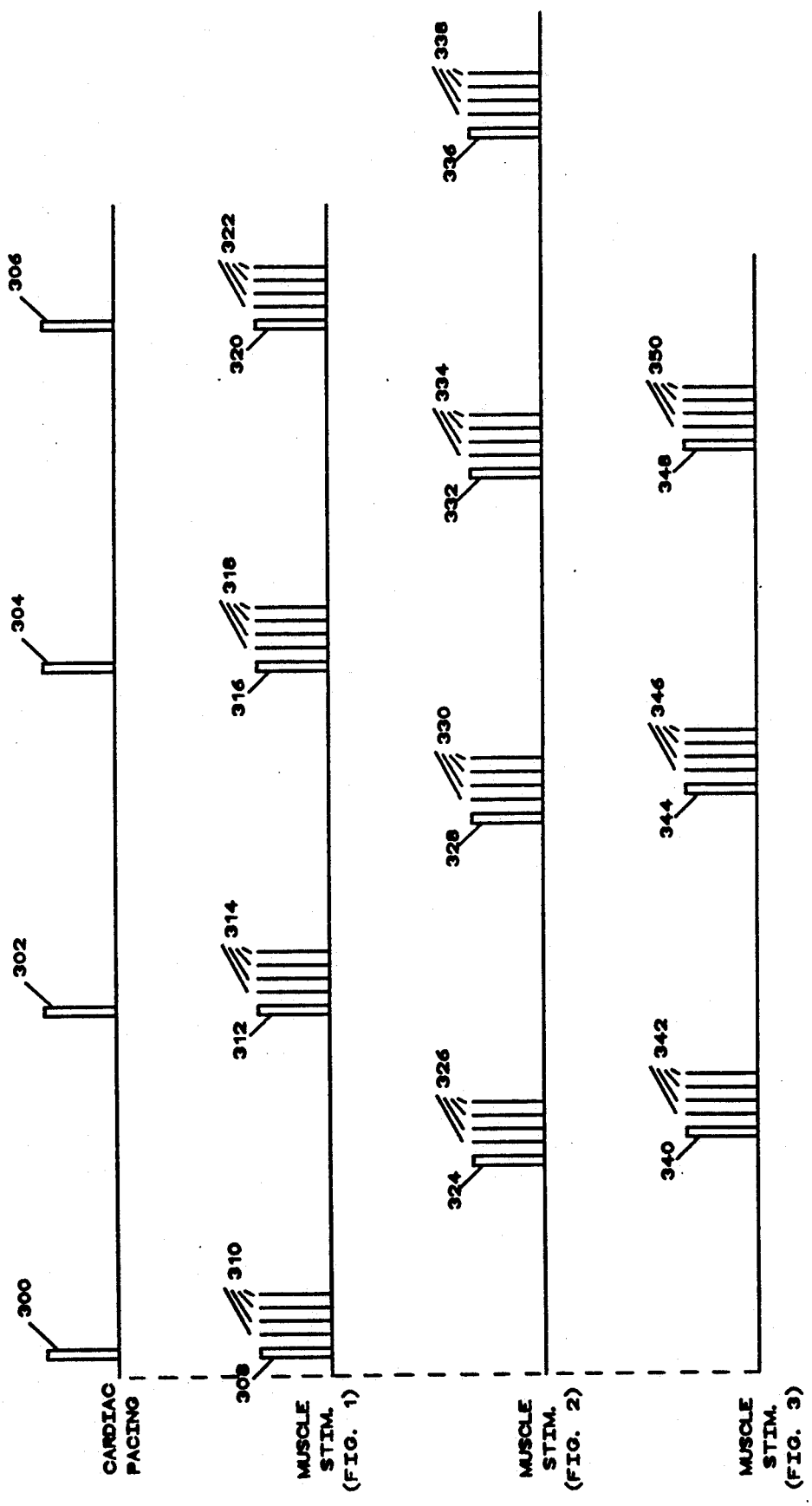
FIG. 8 shows the timing relationship between the cardiac pacing pulse and the skeletal muscle stimulation signals for the embodiments of FIGS. 1, 2, and 3.

FIG. 8 shows the timing relationship between stimulation of the myocardium and stimulation of skeletal muscle 22 for the various embodiments of FIGS. 1, 2, and 3. For simplicity it is assumed that all myocardial contractions are artificially stimulated by pacing pulses 300, 302, 304 and 306 at a fixed rate. These might also be natural contractions which inhibit the pacing pulse, but the rate would then not be constant.

For the embodiment of FIG. 1, it is desired that human heart 100 and skeletal muscle contract simultaneously. Therefore, stimulating pulses 308, 312, 316 and 320 occur at the same time as pacing pulses 300, 302, 304 and 306, respectively. Maintenance pulse groups 310, 314, 318 and 322 occur as explained above. The timing for this embodiment is easily accomplished for paced beats of human heart 100, since the timing is coincident. For sensed beats (i.e., the artificial pacing pulses are inhibited), stimulating pulses 308, 312, 316 and 320 are generated immediately upon sensing a naturally occurring R-wave.

Skeletal muscle 22 is stimulated by pulses 324, 328, 332 and 336 for the embodiment of FIG. 2. These are delayed for a period following the corresponding pacing pulse (or sensed R-wave) sufficient to enable human heart 100 to empty. Contraction of skeletal muscle 22 too soon will increase the load on human heart 100. A delay which is too long will cause skeletal muscle 22 to pump less than the optimal quantity of blood. The exact delay is easily measured by pressure sensor 106 as explained above. The delay may be made a function of rate, stroke volume, etc. It may be determined empirically by medical personnel or simply programmed to the nominal values known in the art.

Stimulation pulses 340, 344 and 348 cause skeletal muscle 22 to counterpulse the descending aorta. This increases the total perfusion through the coronary system, thereby assisting human heart 100. These pulses are timed to occur approximately one-half heart cycle after contraction of human heart 100.

Having thus described the preferred embodiments of the present invention, those of skill in the art will be able to readily apply these to various configurations without deviating from the scope of the following claims.

We claim:

1. A cardiac assist system for assisting a natural human heart having ventricles which contract at a ventricular rate comprising:
   a. a surgically prepared skeletal muscle adapted to be mechanically coupled to said natural human heart such that contraction of said surgically prepared skeletal muscle assists said natural heart;
   b. means responsively coupled to said surgically prepared skeletal muscle for stimulating said skeletal muscle to cause a contraction in synchrony with contraction of said ventricles of said natural human heart; and,
   c. means responsively coupled to said stimulating means and said surgically prepared skeletal muscle for monitoring timing of contractile response of said surgically prepared skeletal muscle relative to the contraction of the ventricle.

2. A cardiac assist system according to claim 1 wherein said monitoring means measures time of occurrence of said contraction.

3. A cardiac assist system according to claim 1 wherein said stimulating means further comprises means for conditioning said surgically prepared skeletal muscle.

4. A cardiac assist system according to claim 3 wherein said monitoring means includes means for making a determination of the effect of said conditioning means.

5. A cardiac assist system according to claim 4 wherein said monitoring means comprises a pressure transducer.

6. A method of assisting a human heart having ventricles which contract at a ventricular rate comprising:

a. surgically wrapping a skeletal muscle about a chamber in fluid communication with said human heart;

b. stimulating said skeletal muscle to contract in timed relation to said ventricles of said human heart; and, c. monitoring said contraction of said skeletal muscle to determine strength of contraction as a function of time.

7. A method according to claim 6 further comprising conditioning said skeletal muscle to minimize fatigue.

8. A method according to claim 7 wherein said monitoring step further comprises monitoring said conditioning step.

9. A method according to claim 6 wherein said monitoring step further comprises monitoring said contraction of said skeletal muscle to ensure that said timed relation is appropriate.

* * * * *